United States Patent
Takagi et al.

(10) Patent No.: US 8,361,487 B1
(45) Date of Patent: Jan. 29, 2013

(54) ANT CONTROLLERS AND METHOD FOR APPLICATION THEREOF

(75) Inventors: Kazuhiro Takagi, Osaka (JP); Yasuhiro Wada, Osakasayama (JP); Rikio Yamaguchi, Kawachinagano (JP)

(73) Assignee: BASF Aktiengesellschaft, Ludwigshafen (DE)

( * ) Notice: Subject to any disclaimer, the term of this patent is extended or adjusted under 35 U.S.C. 154(b) by 645 days.

(21) Appl. No.: 10/019,481

(22) PCT Filed: Jun. 28, 2000

(86) PCT No.: PCT/US00/17895
§ 371 (c)(1),
(2), (4) Date: Apr. 4, 2002

(87) PCT Pub. No.: WO01/01781
PCT Pub. Date: Jan. 11, 2001

(30) Foreign Application Priority Data

Jul. 5, 1999 (JP) .................................... 11-190671

(51) Int. Cl.
*A01N 25/04* (2006.01)

(52) U.S. Cl. .......... 424/405; 424/84; 424/409; 424/410; 514/590

(58) Field of Classification Search .................. 514/590; 424/405
See application file for complete search history.

(56) References Cited

U.S. PATENT DOCUMENTS

| 5,484,599 A | * | 1/1996 | Yoder et al. | 424/405 |
| 5,543,573 A | * | 8/1996 | Takagi et al. | 514/590 |
| 5,691,383 A | * | 11/1997 | Thoms et al. | 514/594 |
| 5,886,221 A | * | 3/1999 | Sbragia et al. | 564/44 |
| 6,342,518 B1 | * | 1/2002 | Treacy et al. | 514/427 |

FOREIGN PATENT DOCUMENTS

| EP | 0500111 | * | 8/1992 |
| WO | 9206076 | * | 4/1992 |

OTHER PUBLICATIONS

Metcalf. Destructive and Useful Insects p. 186,187, 1976.*
Metcalf et al. Destructive and Useful Insects p. 186,187, 1962.*
Stefferud, ed, Insects—the year book of agriculture, p. 469-1952.*

* cited by examiner

*Primary Examiner* — Neil Levy
(74) *Attorney, Agent, or Firm* — Novak Druce + Quigg LLP

(57) ABSTRACT

The present invention provides an excellent ant controller for protecting wooden materials such as trees, board fences, sleepers, etc. and structures such as shrines, temples, houses, outhouses, factories, etc. from termites, and for controlling ants doing harm to crops or humans, which contains as active ingredient thereof a hydrazine derivative represented by general formula (I) [wherein A represents one of formulas (II), (III), (IV), and (V), (wherein $R^4$ and $R^5$ are H, $C_1$-$C_6$ alkyl, etc.; X is 1 to 5 substituents selected from H, halogen and (halo) $C_1$-$C_6$ alkyl); $R^1$ is H or $C_1$-$C_6$ alkyl; $R^2$ and $R^3$ are H, OH, $C_1$-$C_6$ alkyl, phenylcarbonyl, etc.; Y is 1 to 5 substituents selected from H, halogen, nitro and cyano; Z is halogen, cyano, $C_1$-$C_6$ alkyl, etc.; and W is O or S]; and a method for application of the ant controller.

31 Claims, No Drawings

ANT CONTROLLERS AND METHOD FOR APPLICATION THEREOF

BACKGROUND OF THE INVENTION

Field of the Invention

The present invention relates to novel ant controller containing a hydrazine derivative as an active ingredient and to a method for application of the ant controller.

RELATED ART

The hydrazine derivatives represented by the formula (I) which can be used as active ingredient of the ant controllers of the present invention are known compounds disclosed in JP-A-5-4958, JP-A-5-17428, JP-A-5-32603, JP-A-5-262712, etc. In these patents, it is described that these derivatives have an insecticidal activity as agrihorticultural insecticides against LEPIDOPTERA such as diamondback moth, rice leafroller, etc., HEMIPTERA such as tea green leafhopper, pear lace bug, etc., COLEOPTERA such as twenty-eight-spotted ladybird, maize weevil, etc., DIPTERA such as melon fly, house fly, house mosquito, etc., and TYLENCHIDA such as coffee root-lesion nematode, root-knot nematode, etc.

Any of these patent gazettes, however, does neither describe nor suggest that said hydrazine derivatives have a marked insecticidal effect against ISOPTERA such as formosan subterranean termite, kolbe, etc., HYMENOPTERA such as cabbage sawfly, Carpenter ant, etc., ORTHOPTERA such as Japanese cockroach, field cricket, rice grasshopper, etc., and PSOCOPTERA such as large pale booklouse, etc.

SUMMARY OF THE INVENTION

The present inventors have conducted extensive studies with the aim of creating a novel ant controller having a marked controlling effect upon ants doing harm to the wooden materials constituting houses, furniture, etc. or crops and human being. As a result, it has been found that some of the hydrazine derivatives described in the above-mentioned prior art have a marked insecticidal effect upon termites and ants. The present invention has been accomplished on the basis of this findings.

DETAILED DESCRIPTION OF THE INVENTION

The present invention relates to ant controllers containing as active ingredient thereof a hydrazine derivative represented by the following formula (I) and method for application of the ant controllers:

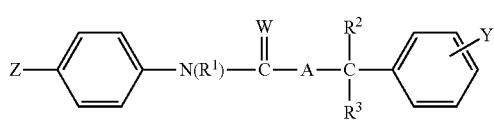

wherein A represents:

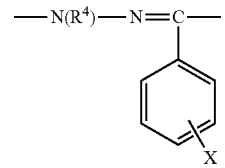

(wherein $R^4$ represents hydrogen atom or $C_1$-$C_6$ alkyl group, and X represents 1 to 5, same or different substituents selected from the group consisting of hydrogen atom, halogen atom, $C_1$-$C_6$ alkyl group and halo $C_1$-$C_6$ alkyl group),

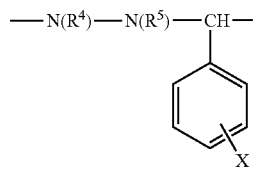

(wherein $R^4$ and X are as defined above, and $R^5$ represents hydrogen atom, $C_1$-$C_6$ alkylcarbonyl group or phenyl-carbonyl group which may have 1 to 2, same or different substituents selected from the group consisting of $C_1$-$C_6$ alkyl groups),

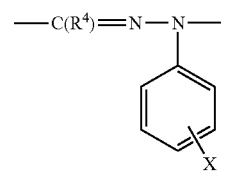

(wherein $R^4$ and X are as defined above), or

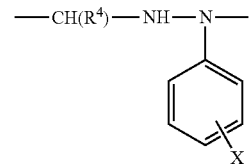

(wherein $R^4$ and X are as defined above);

$R^1$ represents hydrogen atom or $C_1$-$C_6$ alkyl group;

$R^2$ and $R^3$, which may be same or different, represent hydrogen atom, hydroxyl group, $C_1$-$C_6$ alkyl group, $C_1$-$C_6$ alkoxy group, alkylcarbonyl group or phenylcarbonyl group;

Y represents 1 to 5, same or different substituents selected from the group consisting of hydrogen atom, halogen atom, nitro group and cyano group;

Z represents halogen atom, cyano group, $C_1$-$C_6$ alkyl group, halo $C_1$-$C_6$ alkyl group, $C_1$-$C_6$ alkoxy group, halo $C_1$-$C_6$ alkoxy group, halo $C_1$-$C_6$ alkylthio group, halo $C_1$-$C_6$ alkylsulfinyl group or halo $C_1$-$C_6$ alkylsulfonyl group; and W represents oxygen atom or sulfur atom.

The ant controller of the present invention is an excellent ant controller for protecting wooden materials such as trees, board fences, sleepers, etc. and buildings such as shrines, temples, houses, outhouses, factories, etc. from ants such as termites, and for controlling ants doing harm to crops or human being.

In the definition of the formula (I) shown above, the term "halogen atom" means chlorine atom, bromine atom, iodine atom and fluorine atom; the term "$C_1$-$C_6$ alkyl" means a straight or branched chain alkyl group having 1 to 6 carbon atoms; and the term "halo $C_1$-$C_6$ alkyl" means an alkyl group having 1 to 6 carbon atoms substituted with at least one, same or different halogen atoms.

Preferable examples of the hydrazine derivative represented by the formula (I) of the present invention are the hydrazine derivatives represented by the formulas (I-1) and (1-2) as mentioned below. Preferable examples of each substituent of the hydrazine derivatives of formulas (I-1) and (1-2) are the compounds wherein W is oxygen atom, X is trifluoromethyl group, Y is cyano group, Z is trifluoromethoxy group, and each of $R^1$, $R^2$, $R^3$ and $R^4$ is simultaneously a hydrogen atom. More preferable examples are the compounds wherein X is substituted on the 3-position, and Y is substituted on the 4-position of the phenyl ring.

Most preferable example is the hydrazine derivative represented by the formula (I-1), wherein each of $R^1$, $R^2$, $R^3$ and $R^4$ is simultaneously a hydrogen atom, X is trifluoromethyl group substituted on the 3-position of the phenyl ring, Y is cyano group substituted on the 4-position of the phenyl ring, and Z is trifluoromethoxy group.

Typical examples of the hydrazine derivative represented by the formula (I) used as an active ingredient of the ant controller of the present invention are shown in Table 1 to Table 4, but the present invention is by no means limited to the compounds exemplified herein.

Formula (I-1)

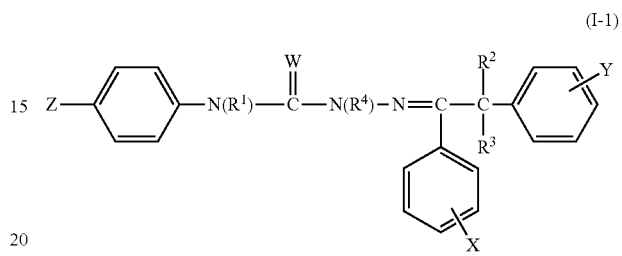

(I-1)

TABLE 1

| No. | $R^1$ | $R^2$ | $R^3$ | $R^4$ | X | Y | Z | W | mp |
|---|---|---|---|---|---|---|---|---|---|
| 1 | H | H | H | H | H | H | Cl | O | 199 |
| 2 | H | H | H | H | H | H | $OCF_3$ | O | 149 |
| 3 | H | H | H | H | H | 4-Cl | Cl | O | 206 |
| 4 | H | H | H | H | H | 4-Cl | $OCF_3$ | O | 197 |
| 5 | H | H | H | H | H | 4-CN | Cl | O | 217 |
| 6 | H | H | H | H | H | 4-CN | Cl | S | 128 |
| 7 | H | H | H | H | H | 4-CN | $OCF_3$ | S | 116 |
| 8 | H | H | H | H | H | 4-CN | $OCF_3$ | O | 214 E-form |
| 9 | H | H | H | H | H | 4-CN | $OCF_3$ | O | 159 Z-form |
| 10 | H | H | H | H | H | 4-$NO_2$ | Cl | O | 222 |
| 11 | H | H | H | H | H | 4-$NO_2$ | Cl | S | 206 |
| 12 | H | H | H | H | H | 4-$NO_2$ | $OCF_3$ | O | 189 |
| 13 | H | H | H | H | H | 4-$NO_2$ | $OCF_3$ | S | 139 |
| 14 | H | H | H | H | H | 4-$NO_2$ | $SCF_3$ | O | 200 |
| 15 | H | H | H | H | 3-Cl | H | $OCF_3$ | O | 212 |
| 16 | H | H | H | H | 3-Cl | 4-Cl | $OCF_3$ | O | 201 |
| 17 | H | H | H | H | 3-Cl | 4-CN | Cl | O | 206 |
| 18 | H | H | H | H | 3-Cl | 4-CN | $OCF_3$ | O | 187 E-form |
| 19 | H | H | H | H | 3-Cl | 4-CN | $OCF_3$ | O | 148 Z-form |
| 20 | H | H | H | H | 3-Cl | 4-CN | $OCF_3$ | S | 199 |
| 21 | H | H | H | H | 3-Cl | 4-CN | $SCF_3$ | O | 215 |
| 22 | H | H | H | H | 3-Cl | 4-CN | $SOCF_3$ | O | 205 |
| 23 | H | H | H | H | 3-Cl | 4-CN | $SO_2CF_3$ | O | 212 |
| 24 | H | H | H | H | 3-Br | H | Cl | O | 191 |
| 25 | H | H | H | H | 3-Br | H | $OCF_3$ | O | 209 |
| 26 | H | H | H | H | 3-Br | 4-CN | Cl | O | 205 |
| 27 | H | H | H | H | 3-Br | 4-CN | $OCF_3$ | O | 176 |
| 28 | H | H | H | H | 3-Br | 4-CN | $SCF_3$ | O | 206 |
| 29 | H | H | H | H | 3-Br | 4-CN | $SOCF_3$ | O | 216 |
| 30 | H | H | H | H | 3-Br | 4-CN | $SO_2CF_3$ | O | 215 |
| 31 | H | H | H | H | 3-F | H | Cl | O | 206 |
| 32 | H | H | H | H | 3-F | H | $OCF_3$ | O | 200 |
| 33 | H | H | H | H | 3-F | 4-Cl | $OCF_3$ | O | 191 |
| 34 | H | H | H | H | 3-F | 4-Cl | Cl | O | 208 |
| 35 | H | H | H | H | 3-F | 4-CN | $OCF_3$ | O | 202 |
| 36 | H | H | H | H | 3-I | 4-CN | Cl | O | 213 |
| 37 | H | H | H | H | 3-I | 4-CN | $OCF_3$ | O | 201 |
| 38 | H | H | H | H | 3-$CH_3$ | H | Cl | O | 185 |
| 39 | H | H | H | H | 3-$CH_3$ | H | $OCF_3$ | O | 198 |
| 40 | H | H | H | H | 3-$CH_3$ | 4-CN | Cl | O | 200 |
| 41 | H | H | H | H | 3-$CH_3$ | 4-CN | $OCF_3$ | O | 189 |
| 42 | H | H | H | H | 3-$CF_3$ | H | Cl | O | 206 |
| 43 | H | H | H | H | 3-$CF_3$ | H | $OCF_3$ | O | 210 |
| 44 | H | H | H | H | 3-$CF_3$ | 4-CN | $OCF_3$ | O | 191 |
| 45 | H | H | H | H | 3-$CF_3$ | 4-CN | $OCF_3$ | S | 149 |

TABLE 1-continued

| No. | R¹ | R² | R³ | R⁴ | X | Y | Z | W | mp □ |
|---|---|---|---|---|---|---|---|---|---|
| 46 | CH₃ | H | H | H | H | H | Cl | O | 132 |
| 47 | CH₃ | H | H | H | H | H | OCF₃ | O | 108 |
| 48 | H | CH₃ | H | H | H | H | Cl | O | 98 |
| 49 | H | CH₃ | H | H | H | H | Br | O | 85 |
| 50 | H | CH₃ | H | H | H | H | OCF₃ | O | 115 EZ-form |
| 51 | H | CH₃ | H | H | H | H | OCF₃ | O | 95 E-form |
| 52 | H | CH₃ | H | H | H | H | OCF₃ | O | 66 Z-form |
| 53 | H | CH₃ | H | H | H | 4-Cl | Cl | O | 121 |
| 54 | H | CH₃ | H | H | H | 4-Cl | OCF₃ | O | 105 |
| 55 | H | CH₃ | H | H | 3-Cl | 4-CN | Cl | O | 140 |
| 56 | H | CH₃ | H | H | 3-Cl | 4-CN | OCF₃ | O | 98 |
| 57 | H | H | OH | H | H | H | Cl | O | 188 |
| 58 | H | H | OH | H | H | H | OCF₃ | O | 170 |
| 59 | H | H | OH | H | H | 4-Cl | Cl | O | Viscous |
| 60 | H | H | OH | H | H | 4-Cl | OCF₃ | O | 185 E-form |
| 61 | H | H | OH | H | H | 4-Cl | OCF₃ | O | 95 Z-form |
| 62 | H | H | OH | H | H | 4-CN | Cl | O | Viscous |
| 63 | H | H | OH | H | H | 4-CN | OCF₃ | O | 113 |
| 64 | H | H | CH₃ | H | H | H | Cl | O | 164 |
| 65 | H | H | CH₃ | H | H | H | OCF₃ | S | 118 |
| 66 | H | H | OCH₃ | H | H | H | Cl | O | 183 |
| 67 | H | H | OCH₃ | H | H | H | OCF₃ | O | 181 |
| 68 | H | H | OC₃H₇-i | H | H | H | Cl | O | 155 |
| 69 | H | H | OC₃H₇-i | H | H | H | OCF₃ | O | 193 |
| 70 | H | H | OC₄H₉-i | H | H | H | Cl | O | 176 |
| 71 | H | H | OC₄H₉-i | H | H | H | OCF₃ | O | 184 |
| 72 | H | H | O—CO—CH₃ | H | H | H | OCF₃ | O | 182 |
| 73 | H | H | O—CO—Ph | H | H | H | OCF₃ | O | 168 |
| 74 | H | H | OH | CH₃ | H | H | Cl | O | 115 |
| 75 | H | H | OH | CH₃ | H | H | OCF₃ | O | 130 |
| 76 | H | H | H | H | H | 3-F | 4-CN | SCF₃ | O | 214 |
| 77 | H | H | H | H | H | 3-F | 4-CN | SOCF₃ | O | 214 |
| 78 | H | H | H | H | H | 4-F | 4-CN | SO₂CF₃ | O | 165 |
| 79 | H | H | H | H | H | 3-Cl | 4-CN | SOCF₃ | O | 157 |
| 80 | H | H | H | H | H | 3-CF₃ | 4-CN | SCF₃ | O | 215 |
| 81 | H | H | H | H | H | 3-CF₃ | 4-CN | SOCF₃ | O | 210 |
| 82 | H | H | H | H | H | 3-CF₃ | 4-CN | OCF₃ | O | 152 Z-form |
| 83 | H | H | H | H | H | 3-CF₃ | 4-CN | Cl | O | 165 |

Note:
Ph is phenyl group.

Formula (I-2)

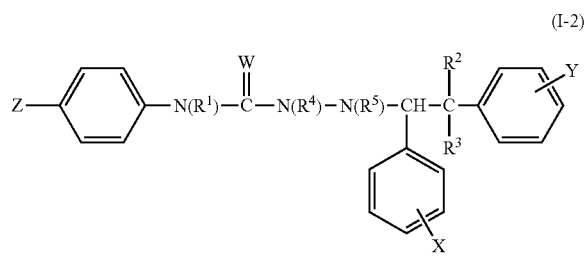

(I-2)

TABLE 2

(R¹ and R³ are hydrogen atoms)

| No. | R² | R⁴ | R⁵ | X | Y | Z | W | mp □ |
|---|---|---|---|---|---|---|---|---|
| 84 | H | H | H | H | H | Cl | O | 211 |
| 85 | H | H | H | H | H | OCF₃ | O | 194 |
| 86 | H | H | H | H | 4-Cl | OCF₃ | O | 209 |
| 87 | H | H | H | H | 4-CN | OCF₃ | O | 204 |
| 88 | H | H | H | H | 4-NO₂ | OCF₃ | O | 203 |
| 89 | H | H | H | 3-F | 4-Cl | OCF₃ | O | 203 |
| 90 | H | H | H | 3-Cl | 4-Cl | OCF₃ | O | 176 |
| 91 | H | H | H | 3-Cl | 4-CN | OCF₃ | O | 193 |
| 92 | H | H | H | 3-Cl | 4-CN | SCF₃ | O | 177 |
| 93 | H | H | H | 3-Cl | 4-CN | SOCF₃ | O | 178 |
| 94 | H | H | H | 3-Cl | 4-CN | SO₂CF₃ | O | 170 |
| 95 | H | H | H | 3-Br | 4-CN | OCF₃ | O | 187 |
| 96 | H | H | H | 3-CF₃ | 4-CN | OCF₃ | O | 165 |
| 97 | H | H | H | 3-CF₃ | 4-CN | SCF₃ | O | 164 |
| 98 | H | H | H | H | 4-Cl | OCF₃ | S | 171 |
| 99 | H | H | H | 3-Cl | 4-CN | OCF₃ | S | 149 |
| 100 | H | H | H | 3-CF₃ | 4-CN | OCF₃ | S | 209 |
| 101 | H | H | CO—CH₃ | 3-Cl | 4-CN | OCF₃ | O | 178 |
| 102 | H | H | CO—Ph | 3-Cl | 4-CN | OCF₃ | O | 221 |
| 103 | H | H | CONHC₂H₅ | 3-Cl | 4-CN | OCF₃ | O | 201 |
| 104 | OH | H | H | H | H | OCF₃ | O | 190 |
| 105 | H | OCH₃ | H | H | H | Cl | O | 195 |
| 106 | H | OCH₃ | H | H | H | OCF₃ | O | 183 |
| 107 | H | OCH₃ | H | H | H | OCF₃ | O | 186 |
| 108 | CH₃ | H | H | 3-Cl | 4-CN | OCF₃ | O | 156 |
| 109 | H | H | H | H | 4-F | OCF₃ | O | 209 |
| 110 | H | H | H | H | 4-Br | Cl | O | 233 |

TABLE 2-continued (R¹ and R³ are hydrogen atoms)

| No. | R² | R⁴ | R⁵ | X | Y | Z | W | mp □ |
|---|---|---|---|---|---|---|---|---|
| 111 | H | H | H | H | 4-Br | OCF₃ | O | 201 |
| 112 | H | H | H | H | 3-CN | OCF₃ | O | 176 |
| 113 | H | H | H | H | 2-NO₂ | OCF₃ | O | 197 |
| 114 | H | H | H | 3-F | 4-CN | OCF₃ | O | 189 |
| 115 | H | H | H | 3-F | 4-CN | SCF₃ | O | 189 |
| 116 | H | H | H | 3-F | 4-CN | SOCF₃ | O | 166 |
| 117 | H | H | H | 3-CF₃ | 4-CN | OCF₃ | O | 131 (−)-Isomer |
| 118 | H | H | H | 3-CF₃ | 4-CN | OCF₃ | O | 126 (+)-Isomer |
| 119 | H | H | H | 3-CF₃ | 4-CN | SOCF₃ | O | Glassy |
| 120 | H | H | H | 3-CF₃ | 4-CN | SO₂CF₃ | O | Glassy |
| 121 | H | H | H | H | 3-CN | OCF₃ | O | 120 |

Note:
Ph is phenyl group.
Compounds 106 and 107 are diastereomers.
Compound 106 is higher than Compound 107 in the Rf value.

Formula (I-3)

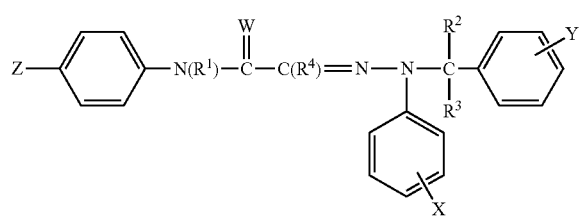

(I-3)

TABLE 3

(R² and R³ are hydrogen atoms, and W is oxygen atom.)

| No | R¹ | R⁴ | X | Y | Z | mp □, Refractive index |
|---|---|---|---|---|---|---|
| 122 | H | H | H | H | OCF₃ | 113.3-114.0 |
| 123 | H | H | H | 4-Cl | OCF₃ | 137.8 |
| 124 | H | H | H | 4-CN | Cl | 163 |
| 125 | H | H | H | 4-CN | OCF₃ | 138 |
| 126 | H | H | 3-Cl | 4-Cl | Cl | 143.5-144.0 |
| 127 | H | H | 3-Cl | 4-Cl | OCF₃ | 139.6-141.5 |
| 128 | H | H | 3-Cl | 4-NO₂ | Cl | 174.0-176.5 |
| 129 | H | H | 3-Cl | 4-NO₂ | OCF₃ | 151.6-151.7 |
| 130 | H | H | 3-Cl | 4-CN | Cl | 191.0-192.0 |
| 131 | H | H | 3-Cl | 4-CN | OCF₃ | 160.5-162.0 |
| 132 | H | H | 3-Cl | 4-CN | SCF₃ | 188.0 |
| 133 | H | H | 3-Cl | 4-CN | SOCF₃ | 206.1 |
| 134 | H | H | 3-F | 4-CN | Cl | 154-156 |
| 135 | H | H | 3-F | 4-CN | OCF₃ | 155.9-156.8 |
| 136 | H | H | 3-CH₃ | 4-CN | Cl | 127 |
| 137 | H | H | 3-CH₃ | 4-CN | OCF₃ | 166 |
| 138 | H | H | 3-CF₃ | 4-CN | Cl | 164-165 |
| 139 | H | H | 3-CF₃ | 4-CN | OCF₃ | 151.0 |
| 140 | H | CH₃ | 3-Cl | 4-CN | OCF₃ | nD 1.5950 (25□□ |
| 141 | CH₃ | H | 3-CF₃ | 4-CN | Cl | 209-211 |
| 142 | H | H | 3-Cl | 2-CN | OCF₃ | 148 |

Formula (I-4)

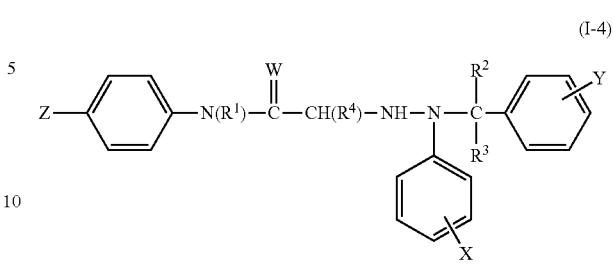

(I-4)

TABLE 4

(R¹, R², R³ and R⁴ are hydrogen atoms.)

| No | X | Y | Z | mp □, Refractive index |
|---|---|---|---|---|
| 143 | H | H | OCF₃ | 51.0-53.0 |
| 144 | H | 4-Cl | OCF₃ | 92.1 |
| 145 | H | 4-CN | Cl | 106-108 |
| 146 | H | 4-CN | OCF₃ | nD 1.5685 (27□) |
| 147 | 3-Cl | 4-Cl | Cl | 105.3-106.4 |
| 148 | 3-Cl | 4-Cl | OCF₃ | 38.0 |
| 149 | 3-Cl | 4-NO₂ | Cl | Viscous |
| 150 | 3-Cl | 4-NO₂ | OCF₃ | Viscous |
| 151 | 3-Cl | 4-CN | Cl | 153.1 |
| 152 | 3-Cl | 4-CN | OCF₃ | 43.5-45.0 |
| 153 | 3-F | 4-CN | Cl | 164-165 |
| 154 | 3-F | 4-CN | OCF₃ | nD 1.5615 (27□) |
| 155 | 3-CH₃ | 4-CN | Cl | 138-139 |
| 156 | 3-CH₃ | 4-CN | OCF₃ | nD 1.5315 (28□) |
| 157 | 3-CF₃ | 4-CN | Cl | 43 |
| 158 | 3-CF₃ | 4-CN | OCF₃ | 153.1 |

Some of the compounds shown in Tables 1 to 4 are viscous or glassy substances. Their ¹H-NMR data are summarized in Table 5.

TABLE 5

| No | ¹H-NMR [CDCl₃/TMS, δ (ppm)] |
|---|---|
| 59 | 6.29 (s, 1H), 7.65-7.92 (m, 13H), 9.14 (bs, 1H), 10.70 (bs, 1H). (DMSO-d₆) |
| 62 | 3.88 (bs, 1H), 3.87 (s, 1H), 6.91-7.55 (m, 13H), 7.73 (s, 1H), 8.13 (bs, 1H). |
| 119 | 3.12 (dd, 1H), 3.23 (dd, 1H), 4.12-4.32 (m, 2H), 6.13 (bs, 1H), 7.24-7.93 (m, 12H), 8.08 (bs, 1H). |
| 120 | 3.11 (dd, 1H), 3.23 (dd, 1H), 4.13-4.28 (m, 2H), 5.97 (s, 1H), 7.25-7.75 (m, 12H), 7.90-8.00 (bs, 1H). |
| 149 | 3.65 (d, 2H), 4.20 (t, 1H), 4.70 (s, 2H), 6.85 (dd, 1H), 6.93 (dd, 1H), 7.08 (dd, 1H), 7.15-7.21 (m, 3H), 7.24 (d, 2H), 7.40 (d, 2H), 8.13 (d, 2H), 8.40 (s, 1H). |
| 150 | 3.64 (s, 2H), 4.69 (s, 2H), 6.84 (dd, 1H), 6.94 (dd, 1H), 7.09 (m, 3H), 7.23 (t, 1H), 7.29 (d, 2H), 7.40 (d, 2H), 8.12 (d, 2H), 8.40 (s, 1H). |

The ant controller of the present invention exhibits a markedly high killing effect at a low dosage upon all the termites doing harm to houses, construction materials, furniture, leathers, fibers, vinyl articles, electric wires and cables, for example, RHINOTERMITIDAE including *Coptotermes formosanus* Shiraki, *Reticulitermes speratus* (Kolbe), *Reticulitermes hesperus* which inhabits the North America, *Reticulitermes tibialis*, *Reticulitermes flavipes*, *Reticulitermes lucifugus* which inhabits the shore of the Mediterranean, *Reticulitermes santonensis*, *Incisitermes minor* (Hagen), TERMITIDAE including *Odontotermes formosanus* (Shiraki), KALOTERMITIDAE including *Cryptotermes domesticus* (Haviland), TERMOPSIME including *Hodotermopsis japonica* (Holmgren), etc.

Further, the ant controller of the present invention exhibits a markedly high killing effect at a low dosage upon all the ants doing harm to crops, or to human being when the ants invade into houses and public facilities such as parks, for example, FORMICIDAE including *Monomorium pharaonis* Linne, *Monomorium nipponense* Wheelex, *Camponotus kiusiuensis* Santschi, *Formica japonica* Motschulsky, *Lasius fuliginosus* (Latreille), *Solenopsis richteri, Solenopsis invicta, Solenopsis geminata* (Fireant), etc.

For using the ant controller of the present invention containing the hydrazine derivative of formula (I) as an active ingredient efficiently, the ant controller is formulated with a proper solid carrier and/or liquid carrier. If necessary, it is formulated with auxiliaries in a proper proportion according to the conventional recipe of formulation, and homogenized together with the carrier by the method of dissolution, suspension, mixing, impregnation, adsorption or adhesion, so as to be made it into an appropriate preparation form such as oily solution, emulsifiable concentrate, solubilized concentrate, dust, granule, wettable powder, aerosol, fumigant, flowable preparation or the like. It is also possible to form the termite controller into a bait preparation by compounding it with a bait containing an attractant or the like.

As the solid carrier used in the present invention, there can be exemplified clays such as kaolin, bentonite, acid clay and the like; talcs such as talc, pyrophillite and the like; silica materials such as diatomaceous earth, siliceous sand, mica, synthetic silicate, synthetic high-dispersion silica and the like; and inorganic mineral powders such as pumice, sand and the like; organic matters such as pieces of wood, chips of pulp wood, grain flour, sugars and the like. As the liquid carrier, there can be exemplified alcohols such as methyl alcohol, ethyl alcohol, ethylene glycol and the like; ketones such as acetone, methyl ethyl ketone, cyclohexanone and the like; ethers such as ethyl ether, dioxane, tetrahydrofuran, *Cellosolves* and the like; aliphatic hydrocarbons such as light oil, kerosene and the like; aromatic hydrocarbons such as benzene, toluene, xylene, solvent naphtha, cyclohexanone, methylnaphthalene and the like; and halogenated hydrocarbons such as chloroform, carbon tetrachloride, chlorobenzene and the like. These solid and liquid carriers may be used either alone or in the form of a mixture.

As the auxiliaries which can be used in the present invention, surfactants, dispersants, sticking agents, etc. can be referred to. As the surfactants, there can be exemplified polyoxyethylene alkylaryl ethers, polyoxyethylene sorbitan monolaurates, alkylaryl sorbitan monolaurates, alkylbenzesulfonates, alkylnaphthalene-sulfonates, ligninsulfonates, higher alcohol sulfuric ester salts, etc. These surfactants may be used either alone or in the form of a mixture.

As the dispersants or sticking agents, for example, casein, gelatin, starch, alginic acid, carboxymethyl cellulose, agar, polyvinyl alcohol, turpentine oil, etc. can be used according to the need.

The ant controller of the present invention is applied not only to the surrounding soil surface or into the under-floor soil in order to protect wooden materials such as trees, board fences, sleepers, etc. and structures such as shrines, temples, houses, outhouses, factories, etc., but it can also be applied to lumbered articles such as surfaces of the under-floor concrete, alcove posts, beams, plywoods, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

The present invention is not limited to the embodiments mentioned above, but it also includes the embodiments of applying the ant controller of the invention preventively to places at which occurrence of ants is expected.

In putting the ant controller of the present invention, the dosage may be appropriately selected from the ranges properly chosen. In case of application to wooden materials, the quantity of active ingredient ranges from 0.1 to 50 g per m$^2$; and in case of soil treatment or application to the nests, the quantity of active ingredient ranges from 1 to 500 g per m$^2$.

EXAMPLES

Next, typical examples and test example of the present invention are presented below. The invention is by no means limited to these examples.

In the examples, "parts" are by weight.

Formulation Example 1

| | |
|---|---|
| Each hydrazine derivative listed in Tables 1-4 | 20 parts |
| Xylene | 80 parts |

The ingredients mentioned above were made into a uniform solution to obtain an oily solution.

Formulation Example 2

| | |
|---|---|
| Each hydrazine derivative listed in Tables 1-4 | 10 parts |
| Polyoxyethylene styrylphenyl ether | 10 parts |
| Cyclohexanone | 80 parts |

The ingredients mentioned above were uniformly mixed and dissolved together to obtain an emulsifiable concentrate.

Formulation Example 3

| | |
|---|---|
| Each hydrazine derivative listed in Tables 1-4 | 10 parts |
| Sodium alkylbenzenesulfonate | 2 parts |
| White carbon | 10 parts |
| Clay | 78 parts |

The ingredients mentioned above were uniformly mixed and pulverized to obtain a wettable powder.

Formulation Example 4

| | |
|---|---|
| Each hydrazine derivative listed in Tables 1-4 | 8 parts |
| Cyclohexanone | 4 parts |

| | |
|---|---|
| Mixture of polyoxyethylene nonylphenyl ether and alkylbenzenesulfonic acid | 3 parts |

A granular composition was prepared by uniformly mixing and dissolving together the ingredients mentioned above, and spraying the resulting solution onto 85 parts of granular pumice, followed by drying.

Test Example 1

A filter paper was spread in a glass dish having a diameter of 9 cm, onto which was dropped 1 ml of a 500 ppm solution of the ant controller of the present invention. Then, the filter paper was inoculated with *Coptotermes formosanus* Shiraki. Seven days after the inoculation, percentage of dead insects was investigated, from which mortality was calculated. The results were evaluated according to the following criterion. The test was carried out with triplicate group of 10 insects.

| Criterion | Mortality (%) |
|---|---|
| A | 100 |
| B | 99-90 |
| C | 89-80 |
| D | 79-50 |

The results are summarized in Table 6.

TABLE 6

| Compound No. | Termite-killing effect |
|---|---|
| 1 | A |
| 2 | B |
| 3 | A |
| 4 | A |
| 5 | A |
| 6 | A |
| 7 | A |
| 8 | C |
| 9 | B |
| 10 | A |
| 11 | A |
| 12 | A |
| 13 | A |
| 14 | A |
| 15 | B |
| 16 | C |
| 17 | A |
| 18 | A |
| 19 | A |
| 20 | A |
| 21 | A |
| 22 | B |
| 23 | A |
| 24 | C |
| 25 | D |
| 26 | A |
| 27 | A |
| 28 | C |
| 29 | C |
| 30 | A |
| 31 | A |
| 32 | A |
| 33 | C |
| 34 | A |
| 35 | A |
| 36 | B |
| 37 | A |
| 38 | B |
| 39 | A |
| 40 | D |
| 41 | A |
| 42 | A |
| 43 | A |
| 44 | C |
| 45 | A |
| 46 | A |
| 47 | A |
| 48 | A |
| 49 | C |
| 50 | A |
| 51 | A |
| 52 | A |
| 53 | B |
| 54 | A |
| 55 | A |
| 56 | A |
| 57 | D |
| 58 | A |
| 59 | C |
| 60 | C |
| 61 | A |
| 62 | A |
| 63 | A |
| 64 | A |
| 65 | C |
| 66 | A |
| 67 | A |
| 68 | A |
| 69 | B |
| 70 | A |
| 71 | A |
| 72 | A |
| 73 | A |
| 74 | A |
| 75 | A |
| 76 | A |
| 77 | A |
| 78 | A |
| 79 | B |
| 80 | A |
| 81 | A |
| 82 | B |
| 83 | D |
| 84 | A |
| 85 | C |
| 86 | A |
| 87 | C |
| 88 | A |
| 89 | B |
| 90 | A |
| 91 | A |
| 92 | A |
| 93 | D |
| 94 | A |
| 95 | A |
| 96 | A |
| 97 | A |
| 98 | A |
| 99 | A |
| 100 | A |
| 101 | A |
| 102 | A |
| 103 | A |
| 104 | A |
| 105 | B |
| 106 | A |
| 107 | D |
| 108 | C |
| 109 | C |
| 110 | B |
| 111 | D |
| 112 | A |
| 113 | A |
| 114 | B |
| 115 | A |

TABLE 6-continued

| Compound No. | Termite-killing effect |
|---|---|
| 116 | B |
| 117 | A |
| 118 | D |
| 119 | A |
| 120 | A |
| 121 | C |
| 122 | D |
| 123 | A |
| 124 | D |
| 125 | A |
| 126 | A |
| 127 | A |
| 128 | A |
| 129 | A |
| 130 | C |
| 131 | C |
| 132 | A |
| 133 | A |
| 134 | A |
| 135 | B |
| 136 | A |
| 137 | A |
| 138 | A |
| 139 | A |
| 140 | A |
| 141 | D |
| 142 | C |
| 143 | C |
| 144 | B |
| 145 | A |
| 146 | D |
| 147 | A |
| 148 | A |
| 149 | A |
| 150 | C |
| 151 | C |
| 152 | B |
| 153 | A |
| 154 | B |
| 155 | A |
| 156 | B |
| 157 | A |
| 158 | C |

Test Example 2

The ant controller of the present invention was applied to nests (anthill) of fireant (*Solenopsis geminata*) with drench treatment, in terms of 1 g of the active ingredient per one nest. 14 Days after the treatment of the ant controller, the activity of the nests was evaluated according to the following criterion. The test was carried out with one block per one nest.

| Criterion | Effect |
|---|---|
| A | Nest is completely destructed or activity of the nest is extremely low. |
| B | Activity of the nest is exhibited. |
| C | High activity of the nest is exhibited. |
| D | Activity of the nest is extremely high. |

As a result of the test, compound Nos. 44 and 96 of the present invention exhibited the effect "A".

What is claimed is:

1. A method for controlling a pest selected from the Isoptera and Hymenoptera orders which comprises applying to the pest or to a wooden part or to soil in the habitat of the pest an effective amount of a hydrazine compound of formula (I-1):

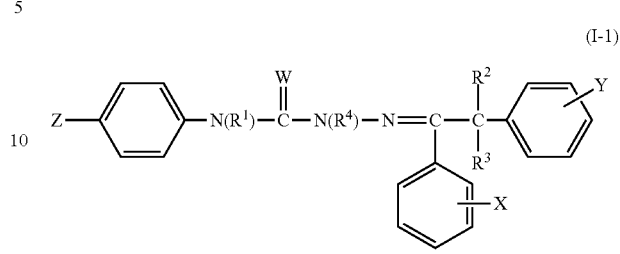

wherein $R^1$, $R^2$, $R^3$, and $R^4$ represent hydrogen;

X represents 1 to 5 same or different halo $C_1$-$C_6$ alkyl substituents;

Y represents 1 to 5 cyano substituents;

Z represents halo $C_1$-$C_6$ alkoxy; and

W represents oxygen, wherein, in case of application to the wooden part, the hydrazine compound is applied in an amount of from 0.1 to 50 g/m$^2$, and in case of application to the pest or the soil, the hydrazine compound is applied in an amount of from 1 to 500 g/m$^2$, and wherein the control results in at least 50% mortality of the pest.

2. The method of claim 1, wherein the hydrazine compound is applied to the wooden part and the pest is selected from the Rhinotermitidae, Termitidae, Kalotermitidae and Termopsidae families.

3. The method of claim 1, wherein X is trifluoromethyl and Z is trifluoromethoxy.

4. The method of claim 3, wherein Y is 4-cyano.

5. The method of claim 1, wherein the hydrazine compound is applied to the pest.

6. The method of claim 1, wherein the pest is an ant or a termite.

7. A method for protecting houses or an article selected from construction materials, furniture, leather, fibers, vinyl articles, electronic wires and cables against a pest selected from the Rhinotermitidae, Termitidae, Kalotermitidae and Termopsidae families, which comprises applying an effective amount of a hydrazine compound of formula (I-1):

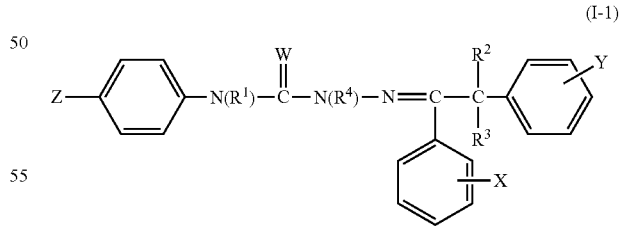

wherein $R^1$, $R^2$, $R^3$, and $R^4$ represent hydrogen;

X represents 1 to 5 same or different halo $C_1$-$C_6$ alkyl substituents;

Y represents 1 to 5 cyano substituents;

Z represents halo $C_1$-$C_6$ alkoxy; and

W represents oxygen, to the pest, a habitat or a nest of the pest, to a place at which occurrence of the pest is expected, or to the article, wherein, in case of application to the pest, the habitat, the nest, or the place, the hydrazine compound is applied in an amount of from 1 to 500 g/m$^2$, and in case of application to the article, the hydrazine compound is applied in an amount of from 0.1 to 50 g/m$^2$, and wherein the protection results in at least 50% mortality of the pest.

8. The method of claim 7, wherein X is trifluoromethyl, Y is 4-cyano, and Z is trifluoromethoxy.

9. The method of claim 7, wherein the hydrazine compound is applied to the pest.

10. A method for controlling a pest from the Formicidae family in crops, which comprises applying an effective amount of a hydrazine compound of formula (I-1):

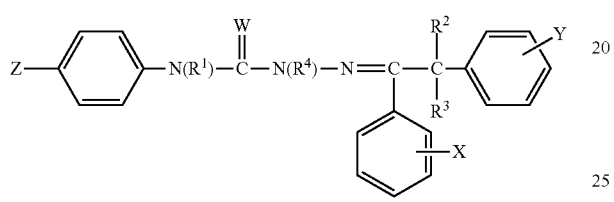

(I-1)

wherein
R$^1$, R$^2$, R$^3$, and R$^4$ represent hydrogen;
X represents 1 to 5 same or different halo C$_1$-C$_6$ alkyl substituents;
Y represents 1 to 5 cyano substituents;
Z represents halo C$_1$-C$_6$ alkoxy; and
W represents oxygen,
to the pest, to the crops, to soil surrounding the crops or to a nest of the pest, wherein the hydrazine compound is applied in an amount of from 1 to 500 g/m$^2$, and wherein the control results in at least 50% mortality of the pest.

11. The method of claim 10, wherein X is trifluoromethyl, Y is 4-cyano, and Z is trifluoromethoxy.

12. The method of claim 10, wherein the hydrazine compound is applied to the pest.

13. A method for protecting wooden materials from termites and ants which comprises applying an effective amount of a hydrazine compound of formula (I-1):

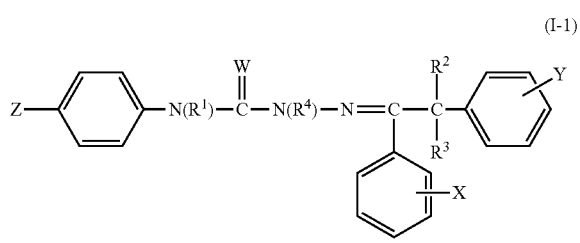

(I-1)

wherein
R$^1$, R$^2$, R$^3$, and R$^4$ represent hydrogen;
X represents 1 to 5 same or different halo C$_1$-C$_6$ alkyl substituents;
Y represents 1 to 5 cyano substituents;
Z represents halo C$_1$-C$_6$ alkoxy; and
W represents oxygen,
to the wooden material, to surrounding soil, or to under-floor soil, wherein from 0.1 to 50 g per m$^2$ of the hydrazine compound is applied and wherein the protection results in at least 50% mortality of the termites and ants.

14. A method for protecting crops from pests of the Formicidae family which comprises applying an effective amount of a hydrazine compound of formula (I-1):

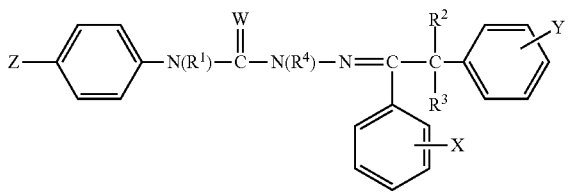

(I-1)

wherein
R$^1$, R$^2$, R$^3$, and R$^4$ represent hydrogen;
X represents 1 to 5 same or different halo C$_1$-C$_6$ alkyl substituents;
Y represents 1 to 5 cyano substituents;
Z represents halo C$_1$-C$_6$ alkoxy; and
W represents oxygen,
to the crops or the surrounding soil or to the nest of the pest, wherein from 1 to 500 g per m$^2$ of the hydrazine compound is applied, and wherein the protection results in at least 50% mortality of the pest.

15. A method for controlling a pest selected from ants and termites of the Isoptera and Hymenoptera orders which comprises applying to the pest or a nest of the pest, or to a wooden part or to soil in the habitat of the pest, an effective amount of a hydrazine compound of formula (I-1):

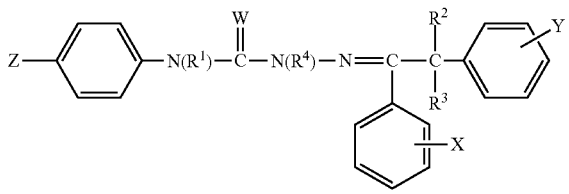

(I-1)

wherein
R$^1$, R$^2$, R$^3$, and R$^4$ represent hydrogen;
X represents 1 to 5 same or different halo C$_1$-C$_6$ alkyl substituents;
Y represents 1 to 5 cyano substituents;
Z represents halo C$_1$-C$_6$ alkoxy; and
W represents oxygen,
wherein, in case of application to the wooden part, the hydrazine compound is applied in an amount of from 0.1 to 50 g/m$^2$, and in case of application to the pest, to the nest or to the soil, the hydrazine compound is applied in an amount of from 1 to 500 g/m$^2$, and wherein the control results in at least 50% mortality of the pest.

16. The method of claim 15, wherein the pest is a termite from the Rhinotermitidae, Termitidae, Kalotermitidae or Termopsidae family, or is an ant from the Formicidae family.

17. The method of claim 15, wherein the pest is a termite from the Rhinotermitidae, Termitidae, Kalotermitidae or Termopsidae family.

18. The method of claim 15, wherein the pest is an ant from the Formicidae family.

19. The method of claim 15, wherein the hydrazine compound of formula (I-1) is applied to the pest in form of a bait preparation.

20. The method of claim 15, wherein the mortality is at least 80%.

21. The method of claim 15, wherein X is a trifluoromethyl group and Y is a trifluoromethoxy group.

22. The method of claim 21, wherein X is in the 3-position of the phenyl ring and Y is in the 4-position of the phenyl ring.

23. A method for protecting a house or an article selected from construction materials, furniture, leather, fibers, vinyl articles, electronic wires and cables against a termite selected from the *Rhinotermitidae, Termitidae, Kalotermitidae* and Termopsidae families, which comprises applying an effective amount of a hydrazine compound of formula (I-1):

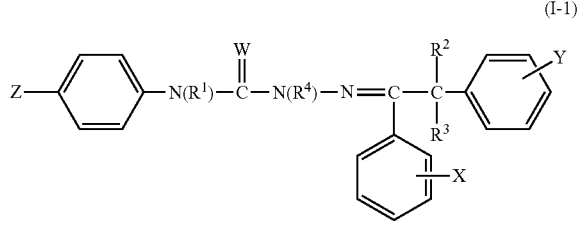

(I-1)

wherein
$R^1$, $R^2$, $R^3$, and $R^4$ represent hydrogen;
X represents 1 to 5 same or different halo $C_1$-$C_6$ alkyl substituents;
Y represents 1 to 5 cyano substituents;
Z represents halo $C_1$-$C_6$ alkoxy; and
W represents oxygen,
to the termite or to the article, or applying from 1 to 500 g/m² of the hydrazine compound of formula (I-1) to a nest of the termite, to soil in the habitat of the termite, to soil in a place where occurrence of the termite is expected, or to under-floor soil or concrete, and wherein the protection results in at least 50% mortality of the termite.

24. The method of claim 23, wherein the hydrazine compound of formula (I-1) is applied to the termite in form of a bait preparation.

25. The method of claim 23, wherein X is a trifluoromethyl group and Y is a trifluoromethoxy group.

26. The method of claim 25, wherein X is in the 3-position of the phenyl ring and Y is in the 4-position of the phenyl ring.

27. A method for controlling an ant from the Formicidae family in crops, which comprises applying an effective amount of a hydrazine compound of formula (I-1):

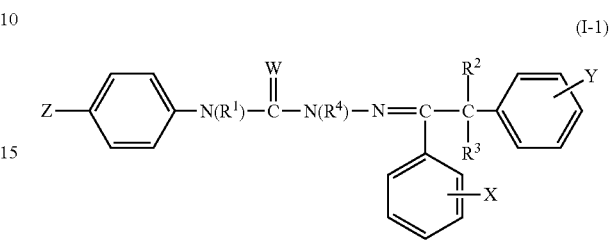

(I-1)

wherein
$R^1$, $R^2$, $R^3$, and $R^4$ represent hydrogen;
X represents 1 to 5 same or different halo $C_1$-$C_6$ alkyl substituents;
Y represents 1 to 5 cyano substituents;
Z represents halo $C_1$-$C_6$ alkoxy; and
W represents oxygen,
to the ant, or applying from 1 to 500 g/m² of the hydrazine compound of formula (I-1) to a nest of the ant, to the crops or to soil surrounding the crops, and wherein the control results in at least 50% mortality of the ant.

28. The method of claim 27, wherein the hydrazine compound of formula (I-1) is applied to the ant in form of a bait preparation.

29. The method of claim 27, wherein the mortality is at least 80%.

30. The method of claim 27, wherein X is a trifluoromethyl group and Y is a trifluoromethoxy group.

31. The method of claim 30, wherein X is in the 3-position of the phenyl ring and Y is in the 4-position of the phenyl ring.

* * * * *